(12) United States Patent
Ogura

(10) Patent No.: US 9,615,741 B2
(45) Date of Patent: Apr. 11, 2017

(54) OPHTHALMOLOGIC IMAGING METHOD, IMAGING APPARATUS, AND NON-TRANSITORY TANGIBLE MEDIUM

(71) Applicant: CANON KABUSHIKI KAISHA, Tokyo (JP)

(72) Inventor: Hiraku Ogura, Tokyo (JP)

(73) Assignee: Canon Kabushiki Kaisha, Tokyo (JP)

( * ) Notice: Subject to any disclaimer, the term of this patent is extended or adjusted under 35 U.S.C. 154(b) by 271 days.

(21) Appl. No.: 14/053,904

(22) Filed: Oct. 15, 2013

(65) Prior Publication Data

US 2014/0104571 A1    Apr. 17, 2014

(30) Foreign Application Priority Data

Oct. 17, 2012    (JP) ................................. 2012-229455

(51) Int. Cl.
    *A61B 3/14*    (2006.01)
    *A61B 3/12*    (2006.01)

(52) U.S. Cl.
    CPC . *A61B 3/14* (2013.01); *A61B 3/12* (2013.01)

(58) Field of Classification Search
    USPC ....... 351/200, 205, 206, 209, 210, 211, 221, 351/222, 243, 244, 245, 246
    See application file for complete search history.

(56) References Cited

U.S. PATENT DOCUMENTS

| | | |
|---|---|---|
| 5,991,028 A | 11/1999 | Cabib et al. |
| 6,769,769 B2 | 8/2004 | Podoleanu et al. |
| 7,980,696 B1 | 7/2011 | Taki et al. |
| 8,472,027 B2 | 6/2013 | Podoleanu |
| 2001/0033364 A1 | 10/2001 | Cabib et al. |

(Continued)

FOREIGN PATENT DOCUMENTS

| | | |
|---|---|---|
| CN | 1694644 A | 11/2005 |
| CN | 102458228 A | 5/2012 |

(Continued)

OTHER PUBLICATIONS

Feb. 16, 2015 Chinese Official Action in Chinese Patent Appln. No. 201310487501.2.

(Continued)

*Primary Examiner* — Joseph P Martinez
*Assistant Examiner* — Brandi Thomas
(74) *Attorney, Agent, or Firm* — Fitzpatrick, Cella, Harper & Scinto

(57) ABSTRACT

In order to perform observation and imaging by the same image capture unit, an ophthalmologic imaging method includes illuminating a fundus of an eye to be inspected with light having a first wavelength, guiding return light from the fundus to an image capture unit through a focus lens so as to obtain an in-focus position of the focus lens in accordance with the light having the first wavelength, illuminating the fundus with light having a second wavelength different from the first wavelength, and guiding return light from the fundus to the image capture unit through the focus lens so as to obtain an image of the fundus. The focus lens is moved to an in-focus position for the light having the second wavelength based on a wavelength difference between the light having the first wavelength and the light having the second wavelength.

23 Claims, 4 Drawing Sheets

(56) References Cited

U.S. PATENT DOCUMENTS

| | | | |
|---|---|---|---|
| 2004/0036838 A1 | 2/2004 | Podoleanu et al. | |
| 2007/0165234 A1 | 7/2007 | Podoleanu | |
| 2011/0051087 A1* | 3/2011 | Inoue | A61B 3/12 |
| | | | 351/206 |
| 2011/0170063 A1* | 7/2011 | Ooban et al. | 351/206 |
| 2011/0176111 A1 | 7/2011 | Taki et al. | |
| 2011/0242373 A1* | 10/2011 | Inoue | H04N 5/3572 |
| | | | 348/242 |
| 2012/0062898 A1 | 3/2012 | Podoleanu | |

FOREIGN PATENT DOCUMENTS

| | | |
|---|---|---|
| JP | H01-178237 A | 7/1989 |
| JP | H02-099032 A | 4/1990 |
| JP | 2007-508558 A | 4/2007 |
| JP | 2011-015955 A | 1/2011 |
| JP | 2011-212240 A | 10/2011 |
| WO | 00/28885 A1 | 5/2000 |

OTHER PUBLICATIONS

Apr. 13, 2016 Chinese Official Action in Chinese Patent Appln. No. 201510320061.0.

* cited by examiner

OPHTHALMOLOGIC IMAGING METHOD, IMAGING APPARATUS, AND NON-TRANSITORY TANGIBLE MEDIUM

BACKGROUND OF THE INVENTION

Field of the Invention

The present invention relates to an ophthalmologic imaging method and apparatus that use a fundus camera or the like, which are used for a physical examination in a group checkup or a general checkup, and to a non-transitory tangible medium therefore.

Description of the Related Art

Conventionally, a fundus examination is performed in a group checkup such as a resident checkup or a company checkup. Usually in fundus imaging in the group checkup, non-mydriatic imaging is performed, which does not need mydriatics. In the non-mydriatic imaging, an examination room is darkened, or a simple darkroom is used so that the eye to be inspected is shielded from indoor light, and thus natural mydriasis of the eye to be inspected is urged for imaging.

An ophthalmologic imaging apparatus that performs non-mydriatic fundus imaging includes an observation light source in an infrared wavelength range that usually does not cause miosis, and a visible imaging light source. In the fundus imaging, the observation light source is used for illuminating the fundus to perform positioning of the imaging apparatus, and then a focus lens is moved to focus on an image capture unit. After that, the imaging light source illuminates the fundus so that an image of the fundus is acquired. However, because observation light and imaging light have different wavelengths, if the observation and the imaging are performed by the same image capture unit, the acquired fundus image has a focus state different from that in the observation. Therefore, an ophthalmologic imaging apparatus, which uses the same image capture unit for observation and imaging, needs a unit for compensating for change of the focus state between observation and imaging caused by the wavelength difference.

As a technique for compensating for the change of the focus state caused by the wavelength difference between the observation light and the imaging light, there is known a fundus camera of Japanese Patent Application Laid-Open No. 2011-015955. The fundus camera of Japanese Patent Application Laid-Open No. 2011-015955 stores a movement amount of a focus lens corresponding to an optical path length difference caused by the wavelength difference between the observation light and the imaging light. When an imaging switch for imaging is depressed after focusing in an observation state, the focus lens is moved by the focus lens movement amount so that the imaging can be performed in an in-focus position for the imaging light.

The imaging method using the fundus camera disclosed in Japanese Patent Application Laid-Open No. 2011-015955 can perform imaging in the same focus state as the observation by moving the focus lens after depressing the imaging switch. However, because it takes time to move the focus lens after depressing the imaging switch, it takes time from the depression of the imaging switch until the imaging by emitting the imaging light. If an involuntary eye movement or a blink of the eye to be inspected occurs during the period, a focus state change or a fundus imaging failure may occur. Therefore, it is desired that the period form the depression of the imaging switch until the imaging be as short as possible.

SUMMARY OF THE INVENTION

The present invention is made in view of the above-mentioned situation, and it is to perform the imaging more quickly so as to reduce a focus state change or an imaging failure due to an involuntary eye movement or a blind of an eye to be inspected.

According to one embodiment of the present invention, there is provided an ophthalmologic imaging method including: illuminating a fundus of an eye to be inspected with light having a first wavelength; guiding return light of the light having the first wavelength from the fundus to an image capture unit through a focus lens; obtaining an in-focus position based on the light having the first wavelength reaching to the image capture unit; illuminating the fundus of the eye to be inspected with light having a second wavelength different from the first wavelength; guiding return light of the light having the second wavelength from the fundus to an image capture unit through the focus lens; and acquiring an image of the fundus based on the light having the second wavelength reaching to the image capture unit, in which the focus lens is moved to an in-focus position for the light having the second wavelength before the fundus is illuminated with the light having the second wavelength, based on a wavelength difference between the light having the first wavelength and the light having the second wavelength.

The ophthalmologic imaging method according to one embodiment of the present invention compensates for a wavelength difference between observation light and imaging light when focus detection is finished. Thus, focus lens movement after depressing an imaging switch becomes unnecessary, and hence the imaging can be performed more quickly. Therefore, the focus state change or the imaging failure due to the involuntary eye movement or the blink of the eye to be inspected may be reduced.

Further features of the present invention will become apparent from the following description of exemplary embodiments with reference to the attached drawings.

DESCRIPTION OF THE EMBODIMENTS

Now, embodiments of the present invention are described in detail with reference to the attached drawings.

First Embodiment

The present invention is described in detail based on an embodiment illustrated in FIG. 1 to FIG. 4.

Figure 1:
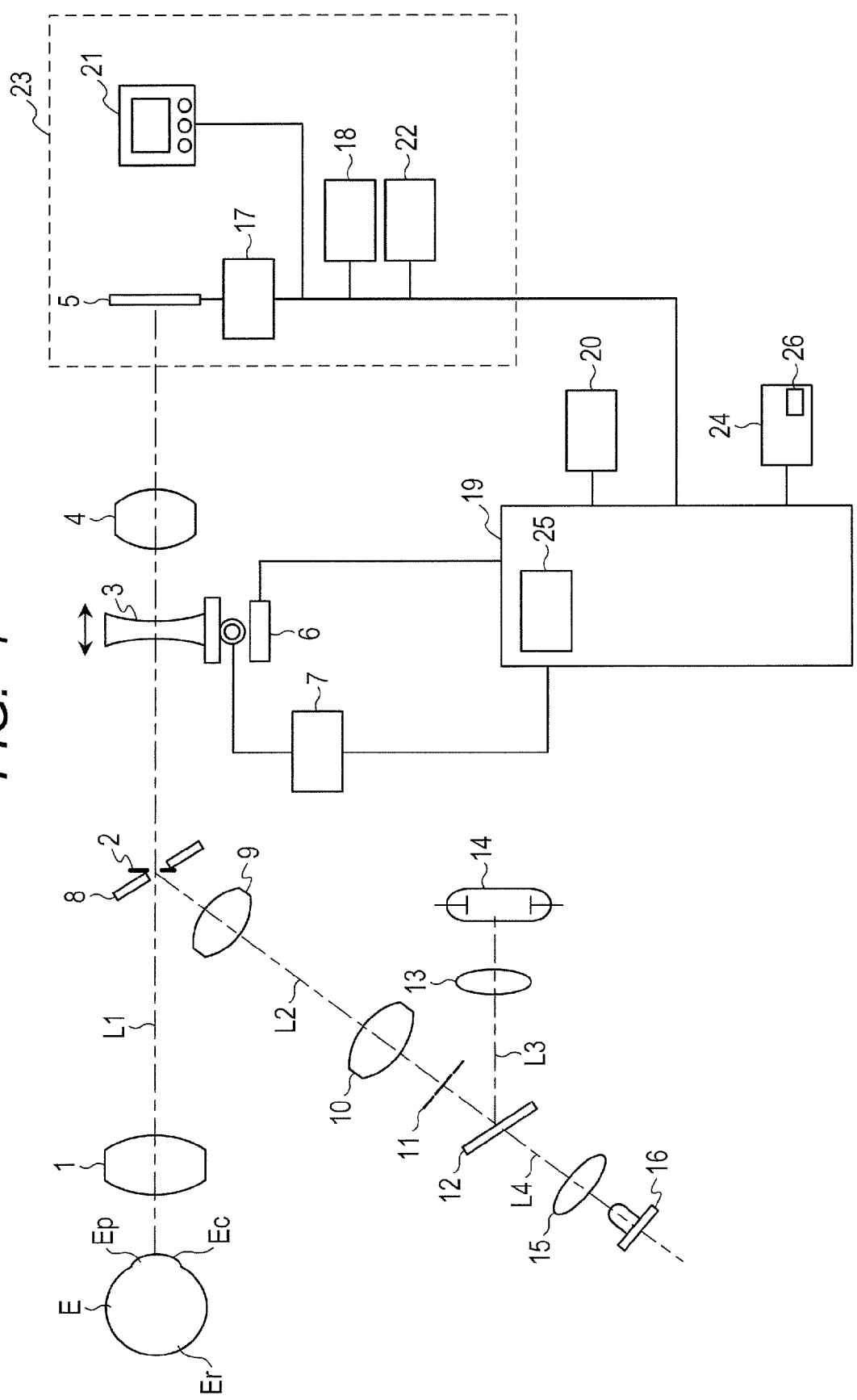
FIG. 1 is a structural diagram of an ophthalmologic imaging apparatus illustrating an embodiment of the present invention.

FIG. 1 is a structural diagram of a fundus camera. An objective lens 1 is disposed to be opposed to an eye to be inspected E. On an optical axis L1 of the objective lens 1, there are disposed an imaging stop 2, a focus lens 3, an imaging lens 4, and an image capture element 5 having sensitivity to visible light and infrared light. The objective lens 1 to the imaging lens 4 constitute an observation/imaging optical system, which constitutes a fundus image observation image capture unit together with the image capture element 5. Note that, the focus lens 3 is connected to a focus lens position detection portion 6 and a focus lens moving portion 7. The focus lens position detection portion 6 outputs a position of the focus lens 3 on the optical axis L1, and the focus lens 3 can be moved on the optical axis L1 by the focus lens moving portion 7.

On the other hand, a perforated mirror 8 is disposed diagonally in a vicinity of the imaging stop 2. On an optical axis L2 in a reflection direction of the perforated mirror 8, there are disposed a lens 9 and a lens 10. In addition, on the optical axis L2, there are disposed a ring stop 11 that is disposed at a position substantially optically conjugate to a pupil Ep of the eye to be inspected E with respect to the lens 9 and the lens and has a ring-like aperture with a light blocking portion in the optical axis center, and a dichroic mirror having characteristics of transmitting infrared light and reflecting visible light. On an optical axis L3 of the dichroic mirror 12 in the reflection direction, there are disposed a condenser lens 13 and a stroboscopic light source 14 as an imaging light source that emits visible pulse light. On an optical axis L4 of the dichroic mirror in the transmission direction, there are disposed a condenser lens 15 and an infrared LED 16 as an observation light source in which multiple infrared LEDs are disposed so as to emit infrared light as infrared stationary light. The objective lens 1 to the dichroic mirror 12, the condenser lens 13, and the condenser lens 15 constitute a fundus illumination optical system. This fundus illumination optical system, the stroboscopic light source 14 as the imaging light source, and the infrared LED 16 as the observation light source constitute a fundus illumination unit. In this embodiment, the stroboscopic light source 14 is a wide-band wavelength light source having a wavelength of 420 nm to 750 nm, and the infrared LED 16 is a single wavelength light source having a wavelength of 850 nm.

The fundus image observation image capture unit and the fundus illumination unit described above are housed in one casing and constitute a fundus camera optical portion. Further, the fundus camera optical portion is placed on a sliding table (not shown) and is capable of being aligned with the eye to be inspected E. Note that, the above-mentioned observation light source corresponds to a first light source for emitting light having a first wavelength for illuminating the fundus in the present invention, and the imaging light source corresponds to a second light source for emitting light having a second wavelength.

In addition, an output of the image capture element 5 is converted into a digital signal by an A/D converter element 17 to be stored in a memory 18, and is connected to a system control portion 19 such as a CPU for controlling the entire apparatus. The system control portion 19 is connected to an image memory 20, and a still image acquired by the image capture element 5 is stored as a digital image. The image capture element 5, the A/D converter element 17, and the memory 18 constitute an image capture unit 23 together with a monitor 21 for displaying an infrared observation image and a visible image acquired by the image capture element 5, and an image capture unit control portion 22. Further, this image capture unit 23 is removably fixed to the casing of the fundus camera optical portion by a mount portion (not shown).

Further, the system control portion 19 is connected to the focus lens position detection portion 6, the focus lens moving portion 7, and an operation input portion 24 so as to control the position of the focus lens 3 on the optical axis L1. Note that, this embodiment is described as an apparatus having an automatic focus function for automatically performing focus adjustment. In a manual focus mode, the movement amount of the focus lens is calculated based on an operation input of the operation input portion 24 and an output of the focus lens position detection portion 6 to control the focus lens moving portion 7. On the other hand, in an automatic focus mode, the focus lens moving portion 7 is controlled based on a result of the detection by a focus detection portion 25 in the system control portion 19 and an output of the focus lens position detection portion 6. In addition, the system control portion 19 also performs control of light amount adjustment and turning on and off of the infrared LED 16 as the observation light, and control of light amount adjustment and turning on and off of the stroboscopic light source 14 as the imaging light.

Next, an operation in this embodiment is described. Light emitted from the infrared LED 16 is condensed by the condenser lens 15 so as to pass through the dichroic mirror 12, and then the light beam is restricted in a ring shape by the ring stop 11. The light restricted by the ring stop 11 once forms an image of the ring stop 11 on the perforated mirror 8 after passing through the lens 10 and the lens 9. In addition, the light is reflected by the perforated mirror 8 in the direction of the optical axis L1. Further, the light forms an image of the ring stop 11 again in a vicinity of the pupil Ep of the eye to be inspected E by the objective lens 1 and illuminates the fundus Er of the eye to be inspected E. In other words, infrared light as the light having the first wavelength of the present invention illuminates the fundus Er of the eye to be inspected E.

The light beam, which is reflected and scattered by the fundus Er illuminated by the light from the infrared LED 16 emitting the stationary light, exits the eye to be inspected E through the pupil Ep. Further, the light beam passes through the objective lens 1, the imaging stop 2, the focus lens 3, and the imaging lens 4, and reaches to the image capture element 5 to form an image. The return light having the first wavelength reflected by the fundus Er, namely first return light is guided to and received by the image capture element 5 as the image capture unit via the focus lens 3. An output from the image capture element 5 is converted into a digital signal by the A/D converter element 17, and then the fundus observation image is displayed on the monitor 21 via the image capture unit control portion 22.

Figure 2A:
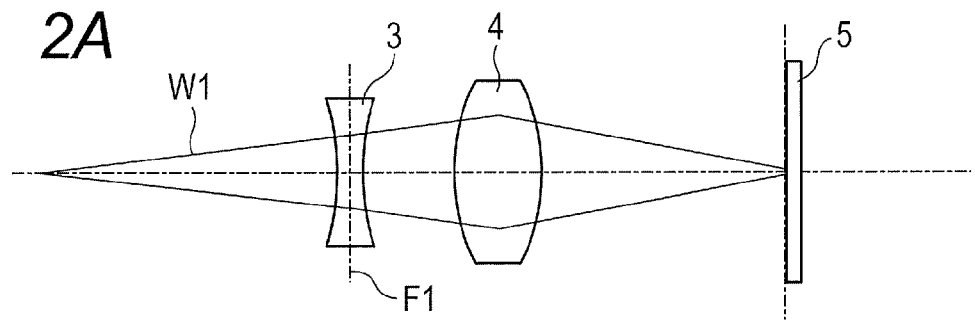
FIGS. 2A, 2B, 2C and 2D are diagrams illustrating focus states of light beams.

The examiner observes the fundus image displayed on the monitor 21 and uses an operation rod (not shown) so as to align the eye to be inspected E with the fundus camera optical portion. If the apparatus is set to the manual focus mode by a focus mode switching unit (not shown), the examiner performs adjustment of the light amount of the infrared LED 16 so that the fundus has an appropriate brightness while observing the fundus image displayed on the monitor 21. In addition, position adjustment of the focus lens 3 in the optical axis L1 direction is performed by the operation input portion 24. FIG. 2A illustrates a state where the focus lens 3 is moved to an observation light in-focus position F1 determined by the examiner so as to be in-focus. In other words, the focus lens 3 is driven based on light having the first wavelength reaching to the image capture unit, and hence the in-focus position, namely the first in-focus position is obtained.

Figure 2B:
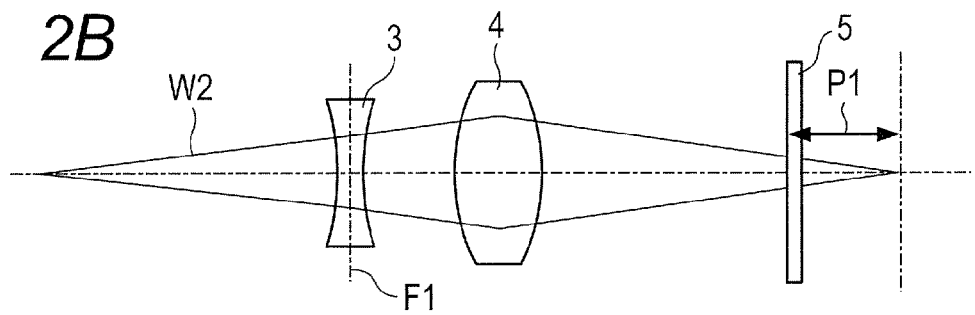

An observation light beam W1 forms an image on the image plane of the image capture element 5 so that a focused fundus image can be observed. Next, the fundus Er of the eye to be inspected E is illuminated with an imaging light beam W2 as light having the second wavelength in a visible range different from the light having the first wavelength. As illustrated in FIG. 2B, the return light of the imaging light beam W2 from the fundus Er is also guided to the image capture element 5 through the focus lens 3, and the image capture element 5 acquires an image of the fundus Er based on the return light as second return light received by the image capture element 5.

However, as illustrated in FIG. 2B, when the fundus Er of the eye to be inspected E is illuminated with the imaging light, an in-focus position difference is caused by an optical path length difference P1 due to the wavelength difference between the observation light and the imaging light. Then, the imaging light beam W2 forms an image at a position different from that of the observation light beam W1, and hence an out-of-focus fundus image is formed on the image plane.

Figure 2C:
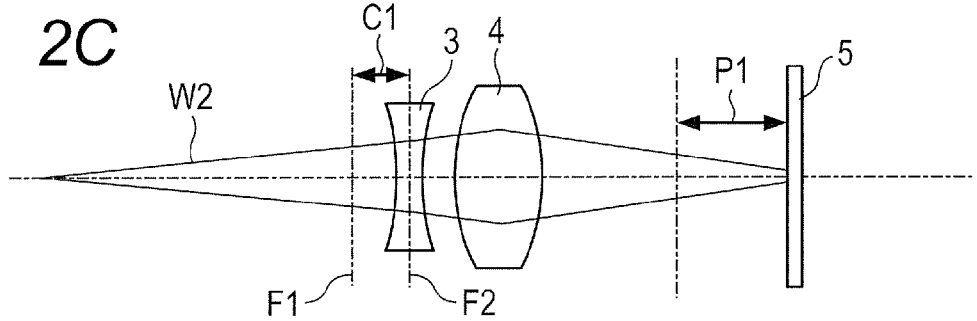

In the focus detection portion 25 of the fundus camera of this embodiment, there is disposed an optical path length compensation unit 25a for storing the movement amount of the focus lens 3 corresponding to the optical path length difference caused by the difference between the wavelength of the infrared LED 16 used as the observation light and the wavelength of the stroboscopic light source 14 used as the imaging light. When start of the imaging is instructed by an imaging switch 26 of the operation input portion 24, based on a compensation value C1 stored in the optical path length compensation unit 25a, as illustrated in FIG. 2C, the focus lens moving portion 7 moves the focus lens 3 to an imaging light in-focus position F2 in accordance with the instruction from the system control portion 19. Next, the stroboscopic light source 14 emits the pulse light, and the light beam emitted from the stroboscopic light source 14 is condensed by the condenser lens 13. After being reflected by the dichroic mirror 12, the light beam is restricted in a ring shape by the ring stop 11. The light beam restricted by the ring stop 11 passes through the lens 10 and the lens 9, and once forms an image of the ring stop 11 on the perforated mirror 8. In addition, the light beam is reflected by the perforated mirror 8 in the direction of the optical axis L1 and forms an image of the ring stop 11 again in a vicinity of the pupil Ep of the eye to be inspected E by the objective lens 1, so as to illuminate the fundus Er of the eye to be inspected E. The light beam reflected and scattered by the fundus Er illuminated by the light beam emitted from the stroboscopic light source 14 exits from the eye to be inspected E through the pupil Ep. This light beam forms an image on the image plane of the image capture element 5 by the focus lens 3 and the imaging lens 4 via the objective lens 1 and the imaging stop 2 as illustrated in FIG. 2C, which is converted into a digital signal by the A/D converter element 17 and is stored as a still image in the image memory 20.

Figure 5:
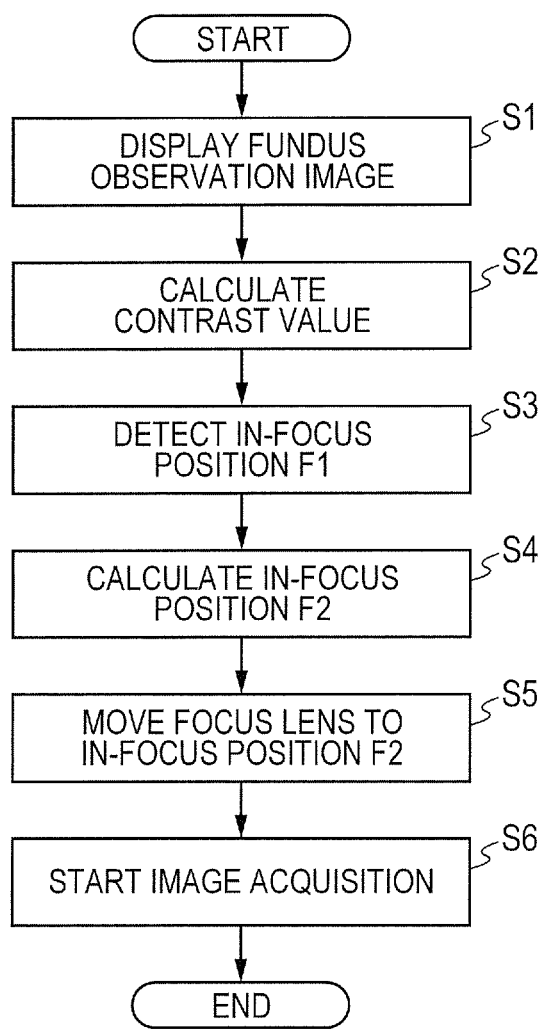
FIG. 5 is a flowchart illustrating an imaging method according to an embodiment of the present invention.

Next, a control method in an automatic focus mode as a feature of this embodiment is described with reference to a flowchart illustrated in FIG. 5. In this embodiment, the focus detection is performed by detecting a contrast value of the fundus image itself formed by the observation light beam. Here, the contrast means a luminance difference between neighboring pixels, and the contrast value is a largest luminance difference value in predetermined luminance data.

Figure 3:
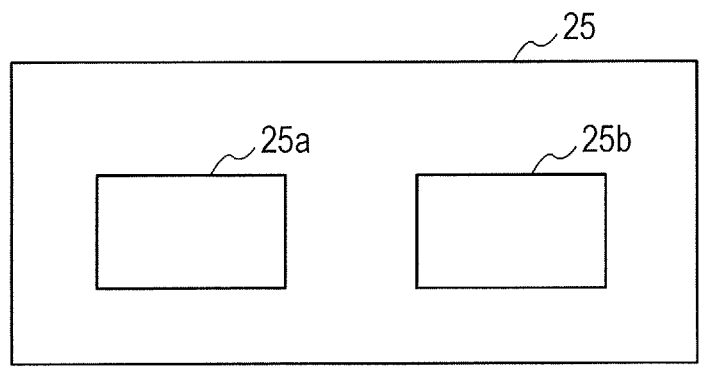
FIG. 3 is a structural diagram of a focus detection portion.
Figure 4:
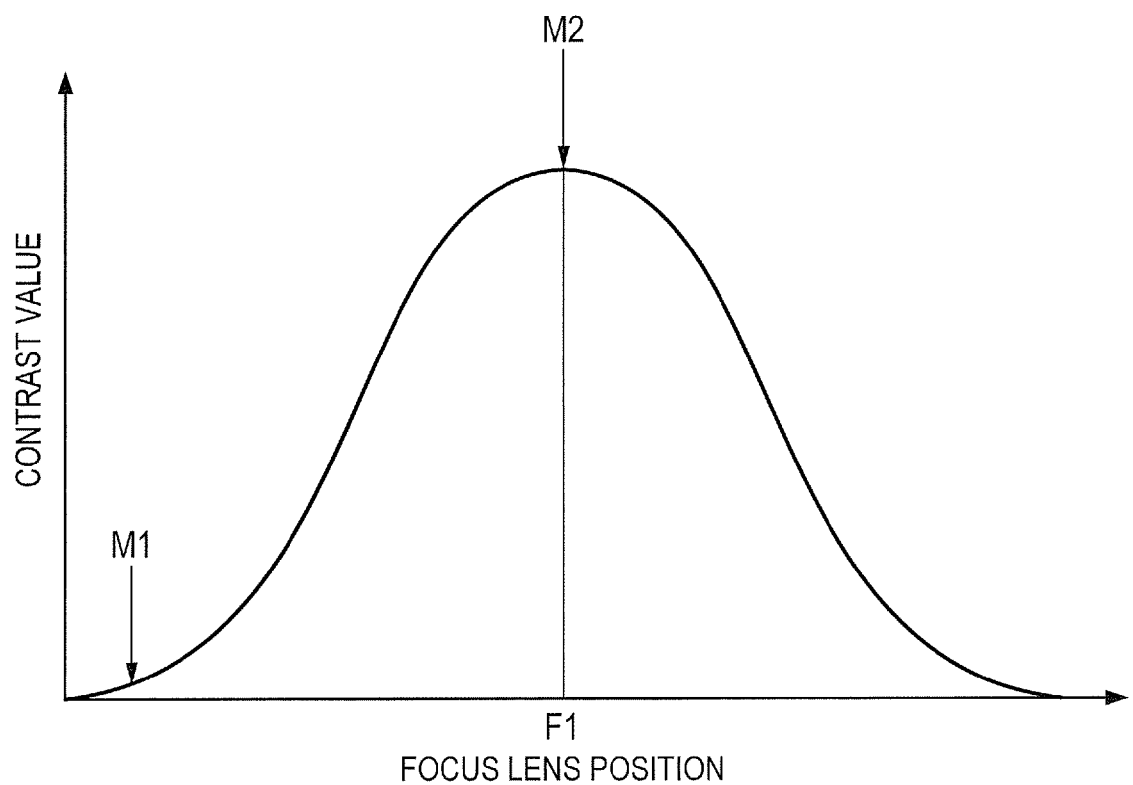
FIG. 4 is a principle diagram of contrast detection.

When start of the automatic focus is instructed by an automatic focus start switch (not shown), the control method is started, and a fundus observation image acquired by the observation light is displayed on a monitor (Step S1). Next in Step S2, calculation of the contrast value in the fundus image of the eye to be inspected is started by the focus detection portion 25 as a focus detection unit of this embodiment. As illustrated in FIG. 3, the focus detection portion 25 includes a focus evaluation value storage unit 25b for storing a contrast value of the fundus image and a position of the focus lens 3. A graph of FIG. 4 shows a transition of the contrast value stored in the focus evaluation value storage unit 25b with respect to a position of the focus lens 3 that is moved by the focus lens moving portion 7 and is output by the focus lens position detection portion 6. As is clear from the graph, the fundus observation image is best in focus at a position M2 having a largest contrast value and is significantly out of focus at a position M1 having a small contrast value, and the fundus image is acquired in this state. Therefore, the position M2 having the largest contrast value in the fundus observation image becomes the observation light in-focus position F1.

The focus detection portion 25 detects the observation light in-focus position F1 as the in-focus position of the focus lens 3 for the light having the first wavelength (Step S3). Based on this observation light in-focus position F1 and the compensation value C1 stored in the optical path length compensation unit 25a, in Step S4, the imaging light in-focus position F2 as the in-focus position for the light having the second wavelength is calculated, and the focus lens 3 is moved to the imaging light in-focus position F2 (Step S5) so as to finish the focusing. The ophthalmologic imaging apparatus having the automatic focus mode can determine that the focus detection is finished. Therefore, the system control portion 19 as a control unit of the present invention performs the calculation of the imaging in-focus position F2 and the movement of the focus lens 3 to the imaging in-focus position F2 promptly after detecting the observation in-focus position F1 regardless of an operation state of the imaging switch 26. In the operation described above, the calculation of the imaging light in-focus position F2 as the second in-focus position is performed by a module region in the system control portion 19, which functions as a calculation unit.

Figure 2D:
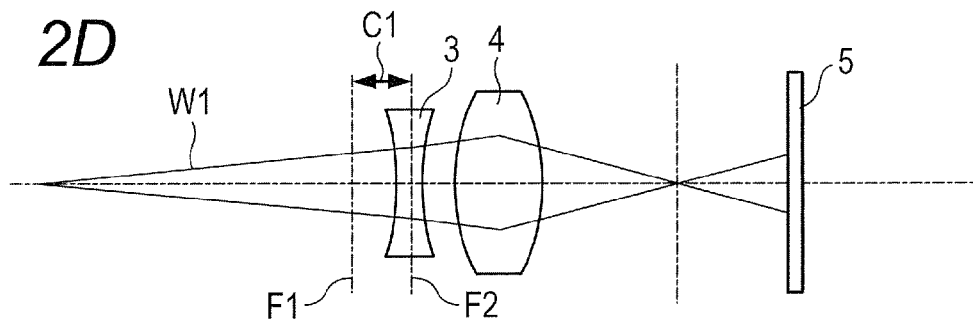

An imaging state in this case is illustrated in FIG. 2D. Because the focus lens 3 is already moved to the imaging light in-focus position F2, the fundus observation image displayed on the monitor 21 at this time is a little out of focus. However, when the examiner depresses the imaging switch 26 in Step S6 to emit light from the stroboscopic light source 14 as the imaging light, the imaging state becomes as illustrated in FIG. 2C, in which an imaging position of the imaging light beam W2 is not deviated from the image plane so that a focused fundus image can be acquired. In addition, the focus lens movement after depressing the imaging switch is not necessary though it is necessary in a manual focus mode. Therefore, the imaging can be performed quickly. Switching from the illumination with the observation light to the illumination with the imaging light described above is performed by a module region in the system control portion 19, which functions as a light source switch unit. The light source switch unit permits switching from the illumination with the light having the first wavelength from the observation light source to the illumination with the light having the second wavelength from the imaging light source after the focus lens 3 moves from the observation in-focus position F1 to the imaging in-focus position F2.

This operation is particularly effective in a non-mydriatic fundus camera that performs observation using infrared light and performs observation and imaging by the same image capture element. In the non-mydriatic fundus camera, in order to prevent miosis of the eye to be inspected in the fundus observation, it is necessary to perform observation with infrared light or the like having a wavelength outside the visible light range. In this case, in order to acquire a stable focused fundus image with the observation light, a compensation unit for the wavelength difference between the observation light and the imaging light is necessary. By moving the focus lens based on the wavelength difference as the compensation unit, a simple structure can be realized because no optical system or mechanism for compensation for the wavelength difference is necessary.

In addition, because the ophthalmologic imaging apparatus having the automatic focus mode can determine an end of the focus detection, movement of the focus lens can be performed after finishing the focus detection. Therefore, because it does not take time to move the focus lens in imaging, quick imaging can be performed.

Other Embodiment

Further, the present invention may also be realized by executing the following process. Specifically, software (program) for realizing the function of the embodiment described above is supplied to a system or an apparatus via a network or an arbitrary type of storage medium, and a computer (CPU or MPU) of the system or the apparatus reads and executes the program.

While the present invention has been described with reference to exemplary embodiments, it is to be understood that the invention is not limited to the disclosed exemplary embodiments. The scope of the following claims is to be accorded the broadest interpretation so as to encompass all such modifications and equivalent structures and functions.

This application claims the benefit of Japanese Patent Application No. 2012-229455, filed Oct. 17, 2012 which is hereby incorporated by reference herein in its entirety.

What is claimed is:

1. An ophthalmologic imaging method comprising:
   illuminating a fundus of an eye to be inspected with light having a first wavelength;
   obtaining a first in-focus position for light having the first wavelength based on return light of the light having the first wavelength from the fundus, the return light of the light having the first wavelength being guided to an image capture unit through a focus lens;
   moving, before instructing by an imaging switch used for acquiring an image of the fundus by illuminating the fundus with light having a second wavelength different from the first wavelength, the focus lens to a second in-focus position for light having the second wavelength based on (a) the first in-focus position and (b) a wavelength difference between the light having the first wavelength and the light having the second wavelength;
   illuminating the fundus of the eye to be inspected with the light having the second wavelength after the instructing by the imaging switch; and
   acquiring an image of the fundus based on return light of the light having the second wavelength from the fundus, the return light of the light having the second wavelength being guided to an image capture unit through the focus lens that had been moved to the second in-focus position.

2. An ophthalmologic imaging method according to claim 1, wherein the obtaining of the first in-focus position is performed in a state where the light having the first wavelength illuminates the fundus.

3. An ophthalmologic imaging method according to claim 1, wherein the image capture unit to which the return light of the light having the first wavelength from the fundus is guided is the same as the image capture unit to which the light having the second wavelength from the fundus is guided.

4. An ophthalmologic imaging method according to claim 1, wherein the light having the first wavelength is infrared light, and wherein the light having the second wavelength is a visible light.

5. An ophthalmologic imaging method according to claim 1, wherein the obtaining of the first in-focus position is performed by detecting a contrast of the fundus.

6. A non-transitory tangible medium having recorded thereon a program for causing a computer to perform steps of the ophthalmologic imaging method according to claim 1.

7. An ophthalmologic imaging method according to claim 1, wherein a difference between the first in-focus position and the second in-focus position is obtained by an optical path length compensation unit that stores in advance an optical path length difference between the light having the first wavelength and the light having the second wavelength based on the wavelength difference.

8. An ophthalmologic imaging method according to claim 1, wherein the step of illuminating the fundus of the eye to be inspected with the light having the second wavelength is executed after the focus lens has been moved to the second in-focus position.

9. An ophthalmologic imaging method according to claim 1, further comprising a step of detecting that the focus lens has been moved to the second in-focus position,
   wherein the step of illuminating the fundus of the eye to be inspected with the light having the second wavelength is executed after the detecting step.

10. An ophthalmologic imaging method according to claim 1, wherein the step of moving the focus lens to the second in-focus position is executed during the step of illuminating the fundus of the eye to be inspected with the light having the first wavelength.

11. An ophthalmologic imaging method comprising:
    illuminating a fundus of an eye to be inspected with light having a first wavelength;
    obtaining a first in-focus position for light having the first wavelength;
    obtaining a second in-focus position for light having a second wavelength different from the first wavelength based on (a) the first in-focus position and (b) a wavelength difference between the light having the first wavelength and the light having the second wavelength;
    moving a focus lens to the second in-focus position before instructing by an imaging switch used for acquiring an image of the fundus by illuminating the fundus with the light having the second wavelength;
    illuminating the fundus of the eye to be inspected with the light having the second wavelength after the instructing by the imaging switch, and
    acquiring an image of the fundus based on the light having the second wavelength.

12. An ophthalmologic imaging method according to claim 11, wherein the step of illuminating the fundus of the eye to be inspected with the light having the second wavelength is executed after the focus lens has been moved to the second in-focus position.

13. An ophthalmologic imaging method according to claim 11, further comprising a step of detecting that the focus lens has been moved to the second in-focus position, wherein the step of illuminating the fundus of the eye to be inspected with the light having the second wavelength is executed after the detecting step.

14. An ophthalmologic imaging method according to claim 11, wherein the step of moving the focus lens to the second in-focus position is executed during the step of illuminating the fundus of the eye to be inspected with the light having the first wavelength.

15. An ophthalmologic imaging apparatus comprising:
a first illuminating unit configured to illuminate a fundus of an eye to be inspected with light having a first wavelength;
an obtaining unit configured to obtain a first in-focus position for the light having the first wavelength and to obtain a second in-focus position for light having a second wavelength different from the first wavelength based on (a) the first in-focus position and (b) a wavelength difference between the light having the first wavelength and the light having the second wavelength;
a moving unit configured to move a focus lens to the second in-focus position before instructing by an imaging switch used for acquiring an image of the fundus by illuminating the fundus with the light having the second wavelength;
a second illuminating unit configured to illuminate the fundus of the eye to be inspected with the light having the second wavelength after the instructing by the imaging switch; and
an acquiring unit configured to acquire an image of the fundus based on the light having the second wavelength.

16. A non-transitory tangible medium having recorded thereon a program for causing a computer to perform steps of the ophthalmologic imaging method according to claim 11.

17. An ophthalmologic imaging method according to claim 11, wherein the light having the first wavelength is infrared light, and wherein the light having the second wavelength is a visible light.

18. An ophthalmologic imaging apparatus according to claim 15, wherein the light having the first wavelength is infrared light, and wherein the light having the second wavelength is a visible light.

19. An ophthalmologic imaging method according to claim 11, wherein both (a) a fundus observation image based on the light having the first wavelength and (b) the image of the fundus based on the light having the second wavelength are acquired by an image capture element capable of sensing a visible light and an infrared light.

20. An ophthalmologic imaging apparatus according to claim 15, wherein both (a) a fundus observation image based on the light having the first wavelength and (b) the image of the fundus based on the light having the second wavelength are acquired by an image capture element capable of sensing a visible light and an infrared light.

21. An ophthalmologic imaging apparatus comprising:
a first illuminating unit configured to illuminate a fundus of an eye to be inspected with light having a first wavelength;
an obtaining unit configured to obtain a first in-focus position for light having the first wavelength based on return light of the light having the first wavelength from the fundus, the return light of the light having the first wavelength being guided to an image capture unit through a focus lens;
a moving unit configured to move, before instructing by an imaging switch used for acquiring an image of the fundus by illuminating the fundus with light having a second wavelength different from the first wavelength, the focus lens to a second in-focus position for light having the second wavelength based on (a) the first in-focus position and (b) a wavelength difference between the light having the first wavelength and the light having the second wavelength;
a second illuminating unit configured to illuminate the fundus of the eye to be inspected with the light having the second wavelength after the instructing by the imaging switch; and
an acquiring unit configured to acquire an image of the fundus based on return light of the light having the second wavelength from the fundus, the return light of the light having the second wavelength being guided to an image capture unit through the focus lens that had been moved to the second in-focus position.

22. An ophthalmologic imaging apparatus according to claim 21, wherein the image capture unit to which the return light of the light having the first wavelength from the fundus is guided is the same as the image capture unit to which the light having the second wavelength from the fundus is guided.

23. An ophthalmologic imaging apparatus according to claim 21, wherein the light having the first wavelength is infrared light, and wherein the light having the second wavelength is a visible light.

* * * * *